US011524104B2

(12) United States Patent
Crnkovich et al.

(10) Patent No.: US 11,524,104 B2
(45) Date of Patent: Dec. 13, 2022

(54) INTEGRATED CROSS CONTAMINATION SENSORS

(71) Applicants: Fresenius Medical Care Deutschland GmbH, Bad Homburg (DE); Fresenius Medical Care Holdings, Inc., Waltham, MA (US)

(72) Inventors: Martin Joseph Crnkovich, Walnut Creek, CA (US); Colin Weaver, Pleasanton, CA (US); Christian Schlaeper, Wehrheim (DE)

(73) Assignees: Fresenius Medical Care Holdings, Inc., Waltham, MA (US); Fresenius Medical Care Deutschland GmbH

( * ) Notice: Subject to any disclaimer, the term of this patent is extended or adjusted under 35 U.S.C. 154(b) by 718 days.

(21) Appl. No.: 16/523,563

(22) Filed: Jul. 26, 2019

(65) Prior Publication Data

US 2021/0023290 A1 Jan. 28, 2021

(51) Int. Cl.
  *G01R 27/06* (2006.01)
  *A61M 1/16* (2006.01)
  *G01N 27/06* (2006.01)

(52) U.S. Cl.
  CPC .......... *A61M 1/1684* (2014.02); *G01N 27/06* (2013.01); *A61M 2205/3317* (2013.01);
  (Continued)

(58) Field of Classification Search
  CPC ........ A61M 1/1684; A61M 2205/3317; A61M 2205/50; A61M 2205/502;
  (Continued)

(56) References Cited

U.S. PATENT DOCUMENTS 6,051,188 A * 4/2000 Spickermann ...... A61M 1/1682
  422/31
2012/0308431 A1* 12/2012 Kotsos ................ A61M 1/1686
  422/105

(Continued)

FOREIGN PATENT DOCUMENTS

CN 107281570 10/2017

OTHER PUBLICATIONS

PCT International Search Report and Written Opinion in International Appln. No. PCT/US2020/040855, dated Nov. 3, 2020, 13 pages.

(Continued)

*Primary Examiner* — Tanmay K Shah
(74) *Attorney, Agent, or Firm* — Fish & Richardson P.C.

(57) ABSTRACT

In some embodiments, a medical system includes a dialysis machine having at least one outer surface to be disinfected at a given location, at least one disinfection sensor connected to the dialysis machine at the given location, the disinfection sensor including two or more electrode in fluid contact with the outside surface of the dialysis machine, and a conductivity sensor component in electrical contact with the two or more electrodes, the conductivity sensor component configured to send an electrical signal indicating a conductivity of a liquid on an outside surface of the dialysis machine and in contact with the two or more electrodes, a processor configured to receive the electrical signal and thereby determine a disinfection status of the given location, and a user interface configured to indicate the disinfection status of the given location.

17 Claims, 9 Drawing Sheets

(52) U.S. Cl.
CPC ... *A61M 2205/50* (2013.01); *A61M 2205/502* (2013.01); *A61M 2205/52* (2013.01); *A61M 2205/584* (2013.01); *A61M 2205/587* (2013.01)

(58) Field of Classification Search
CPC ........ A61M 2205/52; A61M 2205/584; A61M 2205/587; A61M 1/169; A61M 2205/17; A61M 1/28; A61M 1/168; G01N 27/06; G01N 27/07
USPC ....................................................... 324/693
See application file for complete search history.

(56) References Cited

U.S. PATENT DOCUMENTS

| | | | |
|---|---|---|---|
| 2016/0058933 A1* | 3/2016 | Ballantyne .......... | A61M 1/3413 210/85 |
| 2017/0141601 A1* | 5/2017 | Halliburton ........... | H02J 7/0068 |
| 2018/0221555 A1 | 8/2018 | Rohde et al. | |

OTHER PUBLICATIONS

PCT International Preliminary Report on Patentability in International Appln. No. PCT/US2020/040855, dated Feb. 10, 2022, 8 pages.

\* cited by examiner

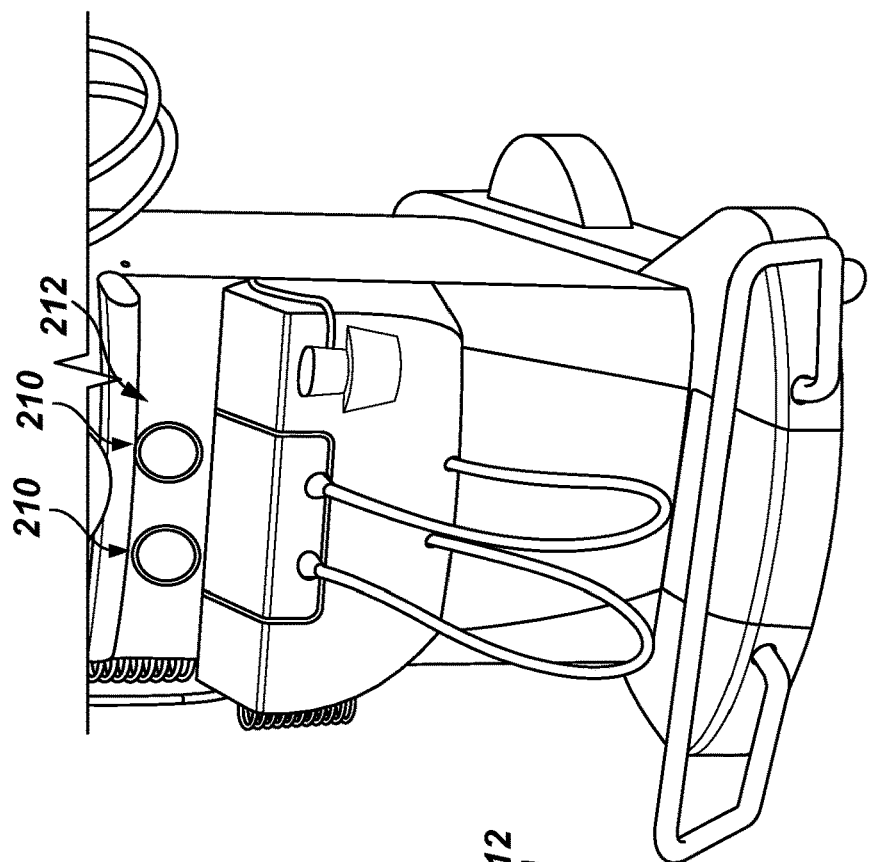
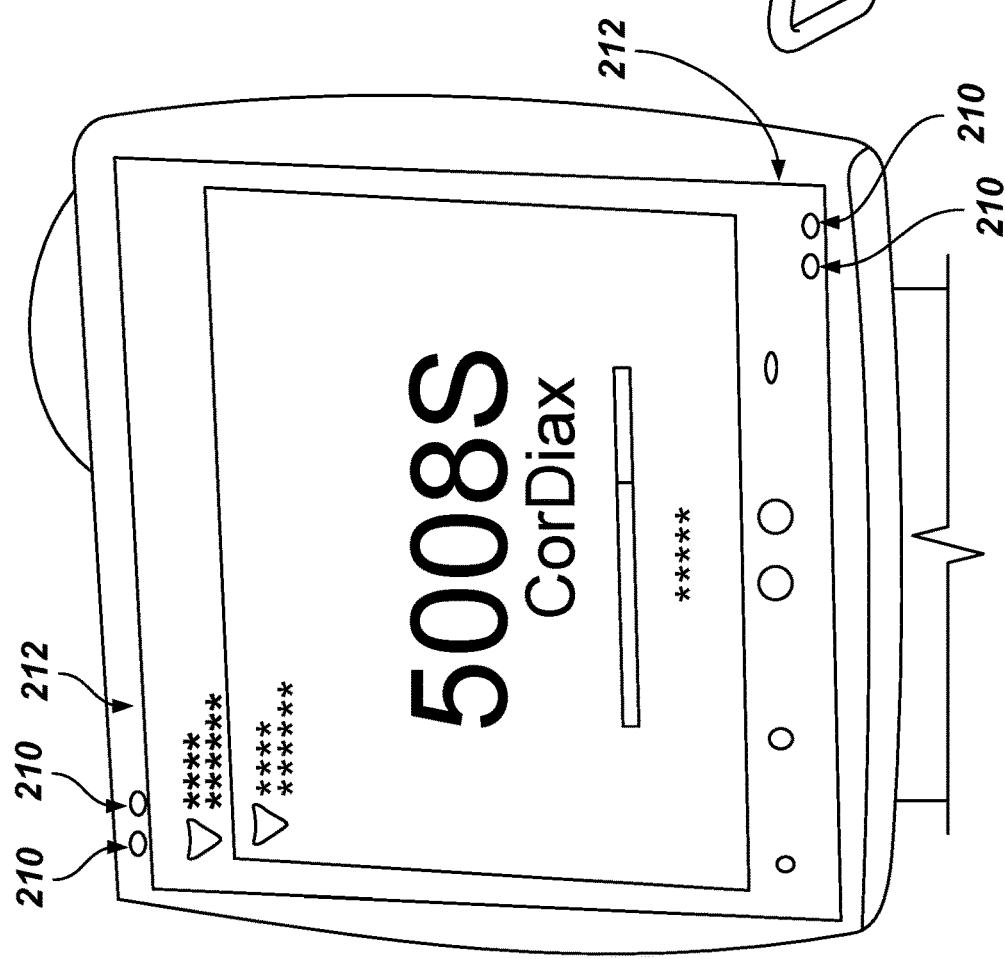
FIG. 2A
FIG. 2B

INTEGRATED CROSS CONTAMINATION SENSORS

TECHNICAL FIELD

This invention relates to detection of contamination.

BACKGROUND

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then discarded.

SUMMARY

This disclosure generally relates to dialysis systems and methods. The dialysis systems include an integrated system that can determine if a durable medical device has been appropriately disinfected. Known methods of infection control include appropriate disinfection of medical devices, specifically frequently-touched surfaces, training and close supervision of all staff in the best practices of infection control, and conducting internal audits to ensure that best practices are followed. Proper disinfection protocols are important for patient outcomes, as approximately 10% of individuals with end-stage renal disease died in 2012 due to infections.

In some embodiments, a medical system includes a dialysis machine having at least one outer surface to be disinfected at a given location, at least one disinfection sensor connected to the dialysis machine at the given location, the disinfection sensor including two or more electrode in fluid contact with the outside surface of the dialysis machine, and a conductivity sensor component in electrical contact with the two or more electrodes, the conductivity sensor component configured to send an electrical signal indicating a conductivity of a liquid on an outside surface of the dialysis machine and in contact with the two or more electrodes, a processor configured to receive the electrical signal and thereby determine a disinfection status of the given location, and a user interface configured to indicate the disinfection status of the given location.

Implementation can include one or more of the following features. Determining a disinfection status of the given location comprises determining if the conductivity signal indicates the liquid on the outside surface of the dialysis machine is a disinfection fluid. Determining if the conductivity signal indicates the liquid on the outside surface of the dialysis machine is a disinfection fluid comprises comparing the conductivity signal to conductivity signals stored in a memory connected to the processor. Determining a disinfection status of the given location comprises determining a time interval the disinfection fluid is present on the outside surface of the dialysis machine. Determining a disinfection status of the given location comprises comparing the time interval to a threshold time interval. Determining a disinfection status of the given location comprises identifying the disinfection fluid present on the outside surface of the dialysis machine. The user interface is configured to alert a user that the machine needs cleaning. A memory that stores a log of disinfections. A cleanable channel on outside surface of the dialysis machine that collects a known amount the liquid.

In some embodiments, a method includes receiving, at a processor, a signal from a conductivity sensor indicating a conductivity of a liquid on an outside surface of a dialysis machine at a given location and in fluid contact with an electrode of the conductivity sensor, determining a disinfection status of the outer surface at the given location, and displaying, on a user interface, the disinfection status of the outer surface at the given location.

Implementation can include one or more of the following features. Determining a disinfection status of the given location comprises determining if the conductivity signal indicates the liquid on the outside surface of the dialysis machine is a disinfection fluid. Determining if the conductivity signal indicates the liquid on the outside surface of the dialysis machine is a disinfection fluid comprises comparing the conductivity signal to conductivity signals stored in a memory connected to the processor. Determining a disinfection status of the given location comprises determining a time interval the disinfection fluid is present on the outside surface of the dialysis machine. Determining a disinfection status of the given location comprises comparing the time interval to a threshold time interval. Determining a disinfection status of the given location comprises identifying the disinfection fluid present on the outside surface of the dialysis machine. Alerting a user that the machine needs cleaning. Storing a log of disinfections in a memory.

Dwell time refers to the required time that a disinfectant must remain wet on a surface to meet the detailed kill claims for specific pathogens.

Advantages of the systems and devices described herein include the use of relatively low-cost, ubiquitous sensors (e.g., disinfection sensors, which can include moisture/wetness sensors, conductivity sensors, chemical sensors, etc.) to ensure appropriate sanitation.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2A-D show locations on a dialysate machine monitor that are to be surface disinfected and their disinfection status monitored by disinfection sensors.

Like reference symbols in the various drawings indicate like elements.

DETAILED DESCRIPTION

An integrated system that can determine if a durable medical device, such as a dialysis machine (e.g., a dialysis machine at a hospital, a home dialysis machine, etc.), has been appropriately disinfected. The system can detect and log that disinfection has occurred, determine what disinfectant was used, determine the dwell time that the disinfectant wetted the machine, determine when the disinfection occurred, determine what sections of the machine were disinfected, determine who disinfected the machine, etc. With this information the medical device can give a clear indication such as an alarm and require proper disinfection protocol be implemented. This information can be used to require the staff to follow the training that they have been given. The information can also be used if an audit of disinfection practices is conducted.

Figure 1:
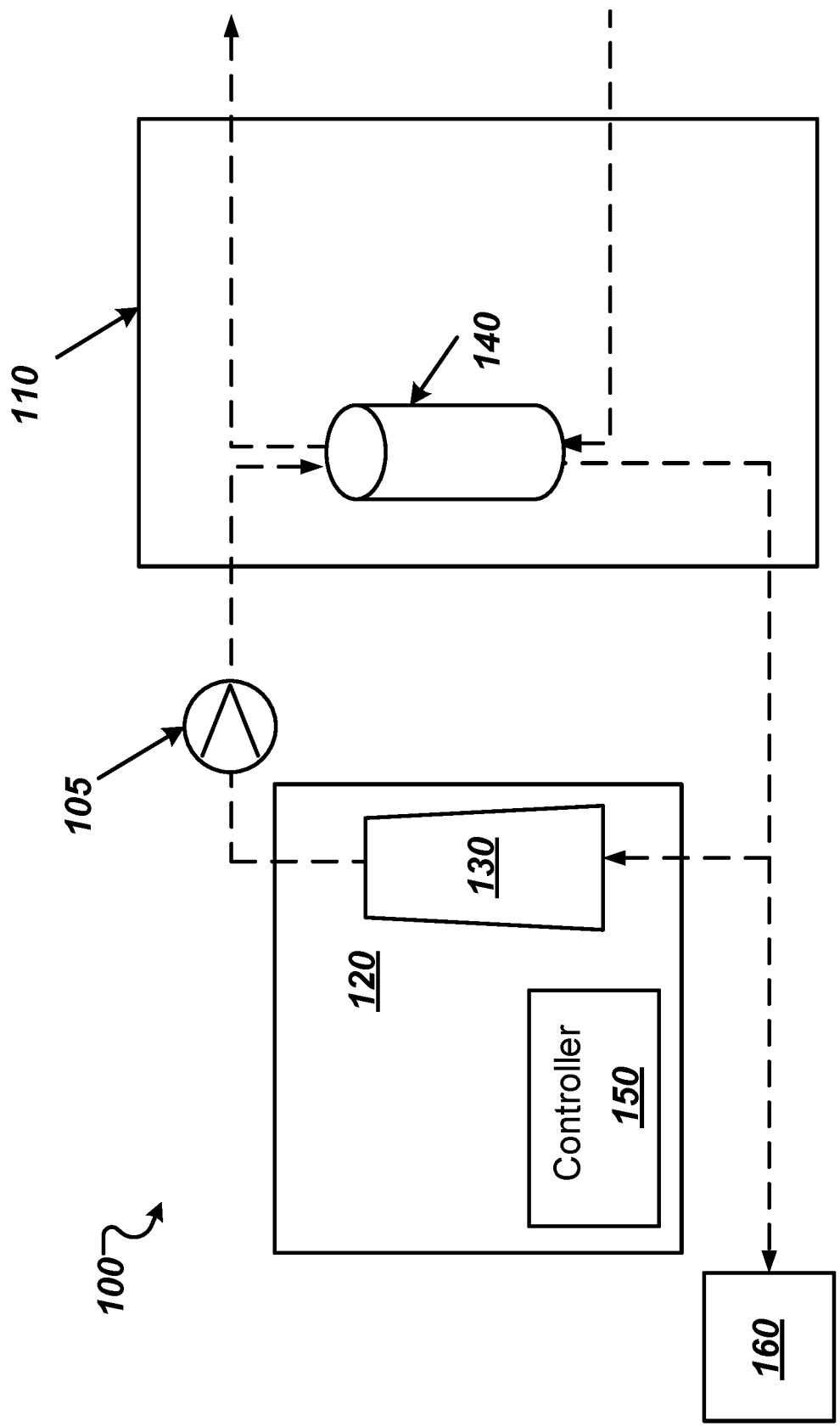
FIG. 1 is a schematic of a dialysis system that includes a dialysis machine.

FIG. 1 shows a high level schematic dialysis system 100 (e.g., a hemodialysis system or a peritoneal dialysis system) in which dialysis solution is moved under the force of at least one pump 105 from a dialysate module 120 to a dialysis machine 110 that includes a dialyzer 140. Once through the dialyzer 140, in some instances the dialysate passes through a sorbent device 130 within the dialysate module 120 and the recycled dialysis solution exits the sorbent device 130 and is moved back to the dialysis machine 110. In some instances, there is no sorbent device 130 and spent dialysate that is generated in the dialysate module 120 and has passed through the dialyzer 140 is directed to a waste container or drain 160. A controller 150 controls the functions of the dialysate module 120.

As the dialysis solution passes through the dialyzer 140 in the dialysis machine 110, toxins are transferred from the patient's blood into the dialysis solution, forming spent dialysis solution. This process can be repeated until a desired amount of toxins have been removed from the patient's blood.

Figure 2C:
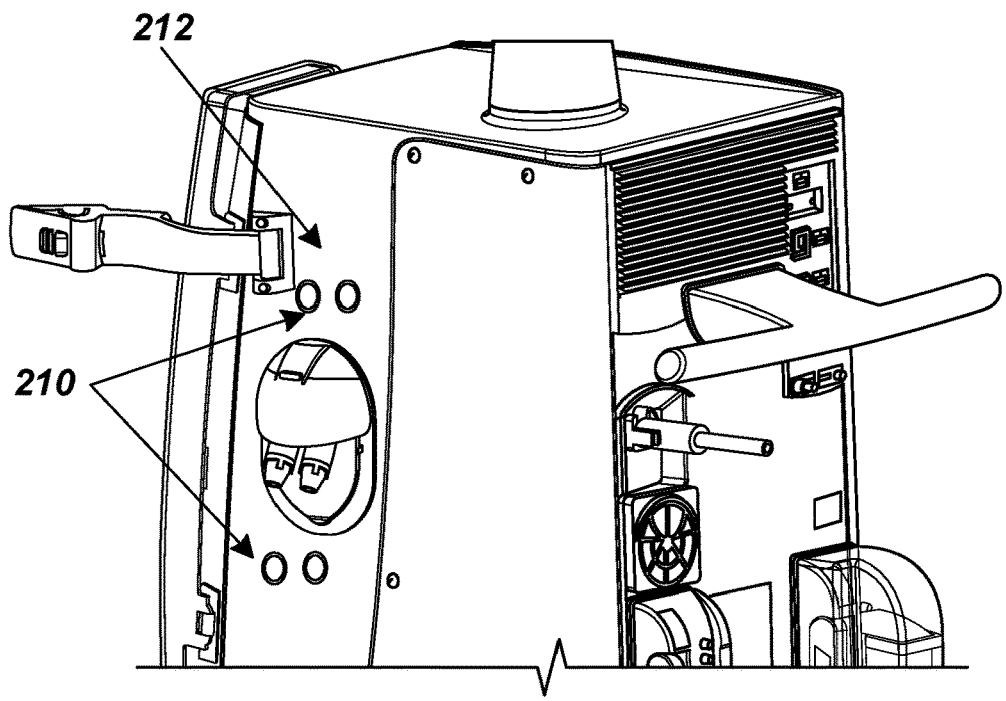
Figure 2D:
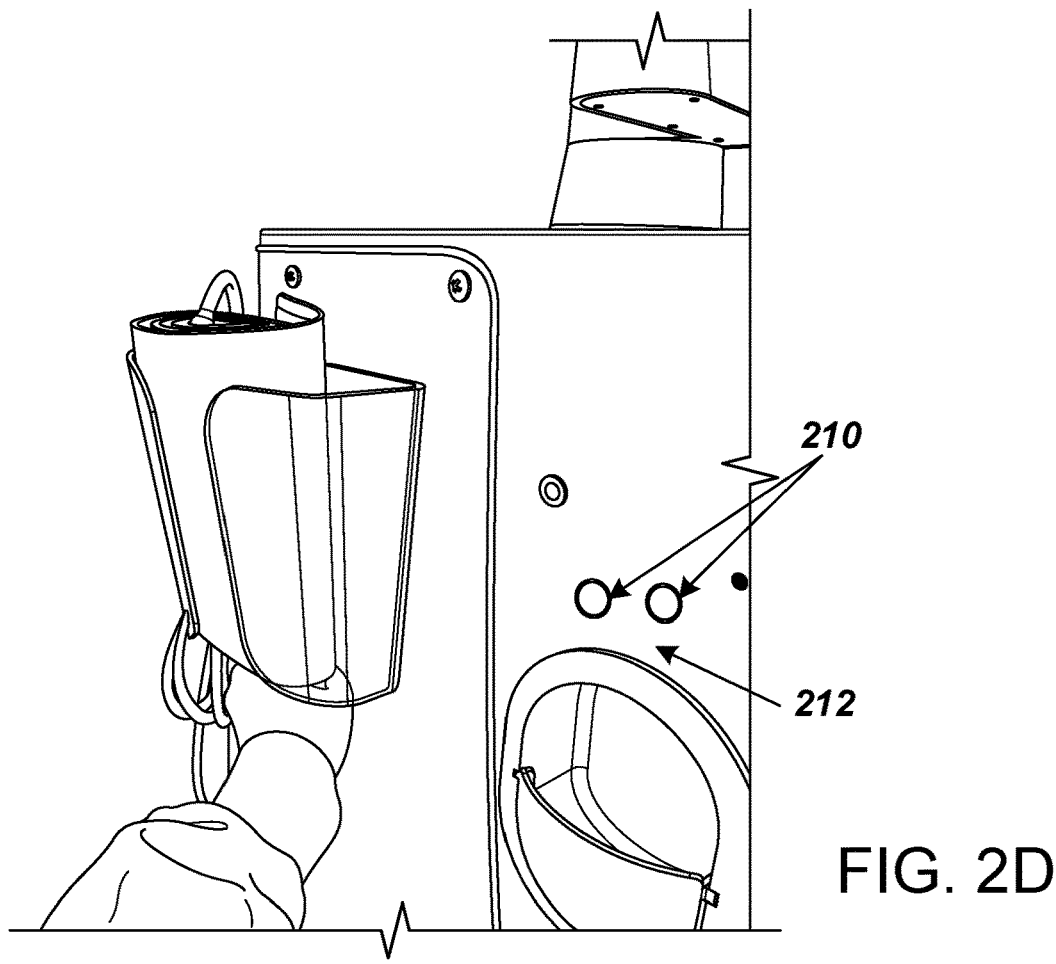

FIGS. 2A-2D show various portions of the dialysis machine 110 that can include small, unobtrusive disinfection sensors 210. These disinfection sensors 210 are placed in areas or locations 212 that require surface disinfections. Multiple disinfection sensors 210 are used as there are several critical locations 212 to be kept disinfected, and the system 100 monitors the disinfected status of all these locations 212 as indicated by the disinfection sensors 210. Locations 212 that have the disinfection sensors 210 include frequently-touched surfaces as well as other surfaces. For example, these locations 212 can include a dialysate machine monitor such as a touch screen (FIG. 2A), a dialysate machine faceplate (FIG. 2B), and sides of the dialysate machine (FIGS. 2C and 2D). The locations 212 may be chosen as places that are especially important to remain clean (e.g., due to typical subsequent touching of the patient) or places that have the potential to become dirty (e.g., due to frequent touching).

Figure 3A:
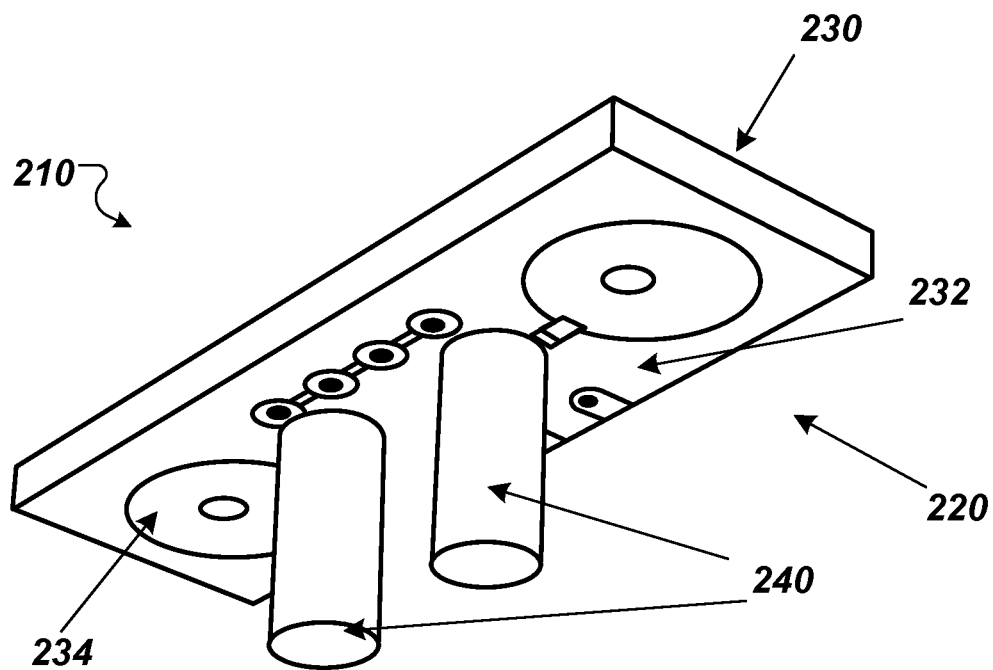
FIG. 3A shows portions of a disinfection sensor that are attachable to the surfaces to be disinfected.
Figure 3B:
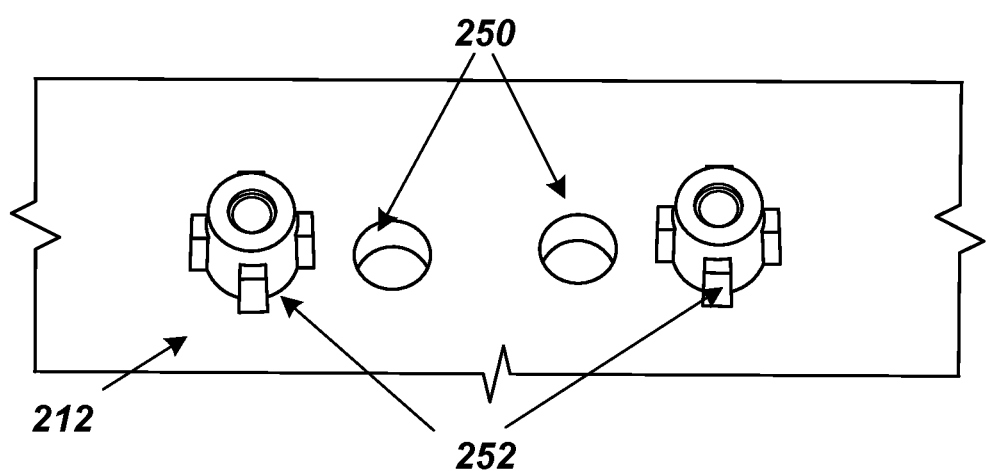
FIG. 3B shows portions of the surface to be disinfected configured for mounting the sensor.
Figure 3C:
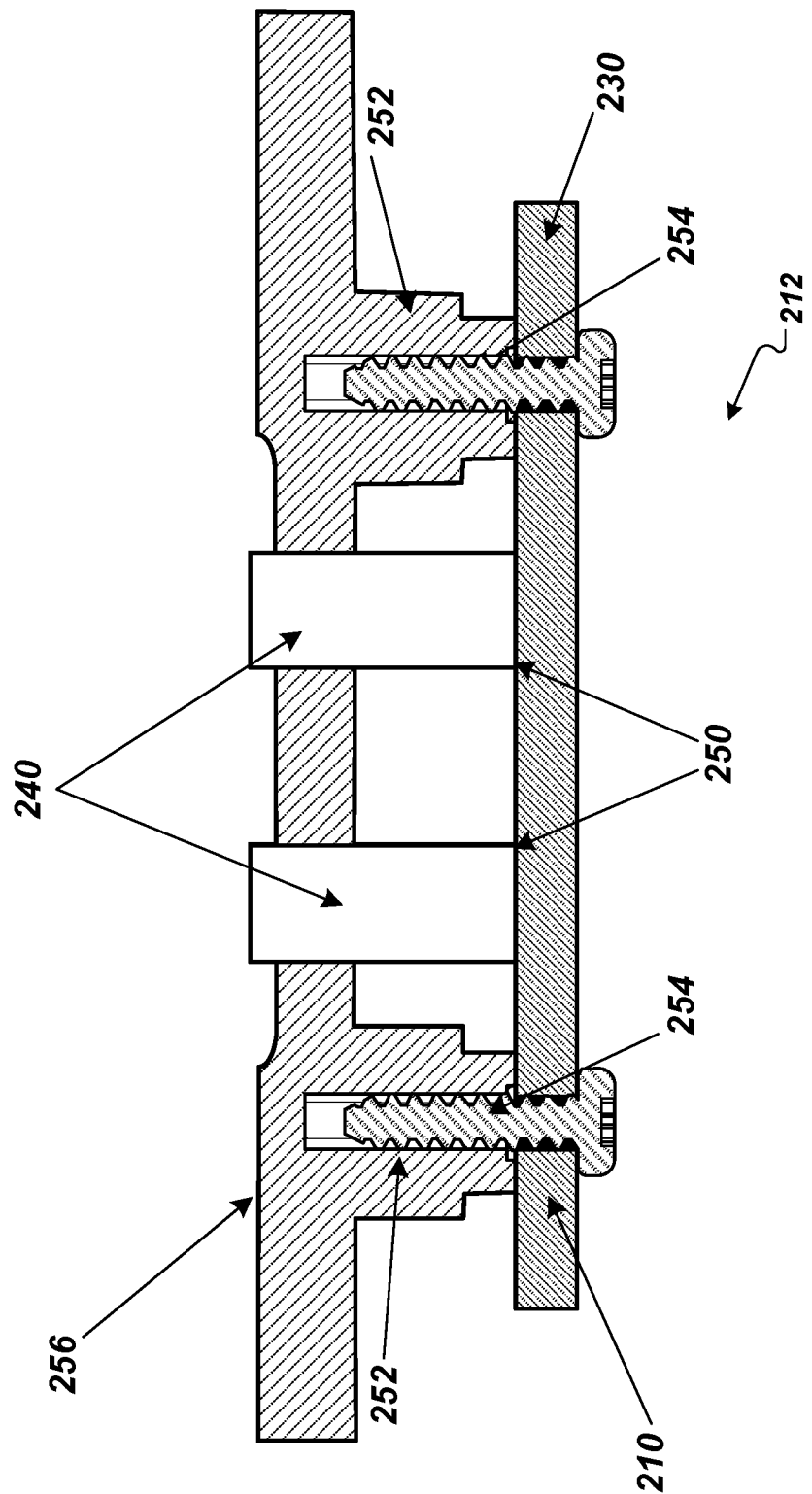
FIG. 3C shows a cross section of portions of the disinfection sensor mounted at a surface to be disinfected.

FIGS. 3A-3C show components of the disinfection sensors 210. The components include attachable portions 220 of the sensors 210 that attach to the surface to be disinfected at each location 212, and portions of the surface itself at the location 212 that are configured to engage with the attachable portions of the disinfection sensors 210.

Referring to FIG. 3A, each disinfection sensor 210 has an attachable portion 220 that includes a small circuit board 230 with connected conductive pins or electrodes 240. The electrodes 240 act as the contact point for the disinfection sensors 210 to the disinfection liquid used to clean the locations 212. Two electrodes 240 are shown, although there can be one, three, four or more such electrodes 240.

The attachable portion 220 of the disinfection sensors 210 can include a wetness sensor component 232, a conductivity sensor component 234, or both a wetness and a conductivity sensor component (as is depicted in FIG. 3A). The circuitry for the wetness sensor component 232 and the conductivity sensor component 234 are located on the circuit board 230. When a dialysis machine 110 is disinfected by having its surfaces wetted by liquid at locations 212 with disinfection sensors 210, the disinfection sensors 210 will detect that the dialysis machine 110 is wet and/or the conductivity of the fluid via the electrodes 240 that are in contact with wetness sensor component 232 and/or the conductivity sensor component 234. The wetness sensor component 232 and/or the conductivity sensor component 234 on the circuit board 230 are connected to a computer, e.g., the controller 150. In some implementations, the conductivity detected by the conductivity sensor component 234 can be used to determine a type of disinfectant being used, for example, hydrogen peroxide, isopropyl alcohol solution, sodium hypochlorite, quaternary ammonium etc. Each of these and other disinfectants are used in different concentrations, for example, 10% hydrogen peroxide or 15%.

One factor that can contribute to high conductivity is residual disinfect left on the surface and then rewetting it. For example if a surface is wiped with a 0.6% sodium hypochlorite solution and then left to sit the water will evaporate and leave behind residual solids. The next time the surface is wiped down with 0.6% sodium hypochlorite solution the residual solids left behind will go into solution and create a higher concentration of sodium hypochlorite solution. The measured conductivity will use thresholds that account for this accumulation. In some instances, controller 150 can include adaptive algorithms that learn and account for this accumulation.

FIG. 3B shows an example of how the surface of the dialysis machine 110 at each location 212 can be configured to mate with attachable portion 220 including the circuit board 230 with connected electrodes 240 shown in FIG. 3A. Each location 212 includes through holes 250 and bosses 252. Nearly any surface of the machine 110 (in particular, surfaces that are plastic) can be adapted to accept the attachable portions 220 FIG. 3A.

Figure 4:
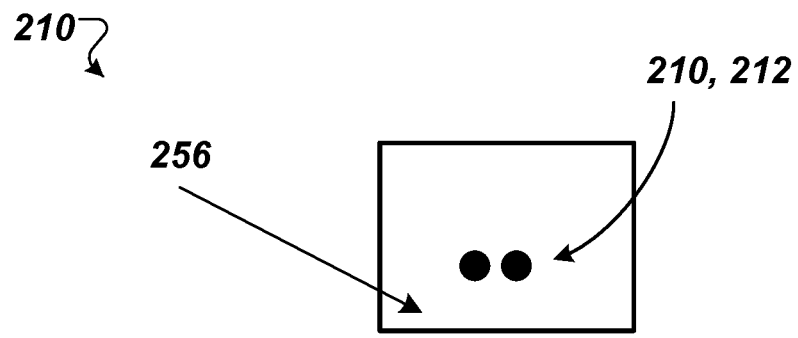
FIG. 4 shows how the disinfection sensor looks from the outer surface.

The cross section of FIG. 3C depicts how the attachable portion 220 is mounted at any given location 212. The holes 250 on the surface of the machine mate with the electrodes 240 of the attachable portion 220, and the bosses 252 on the surface of the machine accept screws 254. The screws 254 (e.g., self-tapping screws) attach the circuit board 230 to the machine surface at the location 212 such that the electrodes 240 protrude through the holes 250 and are visible (and in fluid contact with) the outer surface 256 of the machine at location 212. The electrodes 240 can be flush with the outer surface 256 (e.g., flat). In some instances, the electrodes 240 can protrude past the outer surface 256 such that a portion of the sides of the electrodes 240 extends a distance beyond the outer surface 256 (e.g., less than 1 mm) is not in contact with the outer surface 256. The result is that the sensor 210 is in contact with and visible from the outer surface 256, as shown in FIG. 4.

The disinfection sensors 210 can include a wetness sensor component 232 configured to detect wetness on the outer surface 256 of a given location 212. The wetness sensor component 232 detects that fluid (e.g., a disinfecting agent) is present at the location 212. The disinfection sensor 210 can register the time at which the liquid is detected, and the time at which liquid is no longer detected. These times allow calculation of the dwell time by the controller 150 that the surface is wetted, e.g., time in contact with a disinfection fluid.

In some instances, the controller 150 can include in memory a saved time period against which to compare the calculated dwell time. The saved time period can equal a time that is known, or is recommended, that a surface remain wetted by disinfection fluid for that surface to be considered clean or disinfected. The controller 150 is thus configured to detect that fluid on the surface was wet from an initial time point and remained wet and not dried enough for the disinfecting fluid to be inactive.

In some instances, channels can be positioned in the outer surface 256 so that disinfection fluid becomes trapped in the channels. Such an arrangement ensures that evaporation does not cause the disinfection fluid to not register as meeting the time threshold.

In some embodiments, the disinfection sensor 210 includes a conductivity sensor component 234. When wetted with a disinfection fluid, the electrodes 240 register a change in conductivity that is read by the conductivity sensor component 234. Certain measured conductivity values can be associated with the presence of a disinfection fluid on the outer surface 256. The disinfection sensor 210 can register the time at which the change in conductivity and thereby the disinfection liquid is detected, and the time at which it is no longer detected. These times allow calculation of the dwell time by the controller 150 that the surface is in contact with the disinfection fluid.

In some instances, the controller 150 can include in memory a saved time period against which to compare the calculated dwell time. The saved time period can equal a time that is known, or is recommended, that a surface remain wetted by a disinfection fluid for that surface to be considered clean or disinfected.

In some embodiments, the controller 150 can correlate the conductivity value measured the disinfection sensor 210 with the conductivity of a known disinfection fluid. For example, the controller 150 can include a memory that stores a look-up table that contains the conductivity values of a range of commonly used disinfectants, (e.g., bleach). By comparing the measured conductivity value with the stored conductivity values, the controller 150 can thereby determine which disinfection fluid was used.

The concentration of the disinfection fluid changes as the applied fluid dries and evaporates from the outer surface 256. The controller 150 can include information correlating a range of conductivity measurement to a known disinfection fluid. In some instances, the disinfection fluid used can be selected so that the needed dwell time is short, e.g., less than 3 minutes. In such an instance the conductivity measurements are not affected during the period of time the surface is wetted since not enough water will evaporate to change the concentration of the disinfection fluid.

In some instances, channels can be positioned in the outer surface 256 so that disinfection fluid becomes trapped in the channels. Such an arrangement ensures that evaporation does not cause the disinfection fluid to not register as meeting the time threshold.

There can be multiple locations 212 on the dialysis machine 110. Some of the locations 212 will be horizontal whereas some will not and no not be able to make use of gravity to fill a surrounding channel and hold the fluid in place while the conductivity measurement is taken. In such instances, a single conductivity reading can be taken in a single horizontal location. The rest of the sensors at other locations 212 can simply be wetted and the system can assume that the same disinfectant and dwell time were employed as at the horizontal, representative location.

FIG. 4 shows how the disinfection sensor 210 looks from the outer surface 256. In this example, only the end portions of the electrodes 240 are visible on the outer surface 256.

Figure 5:
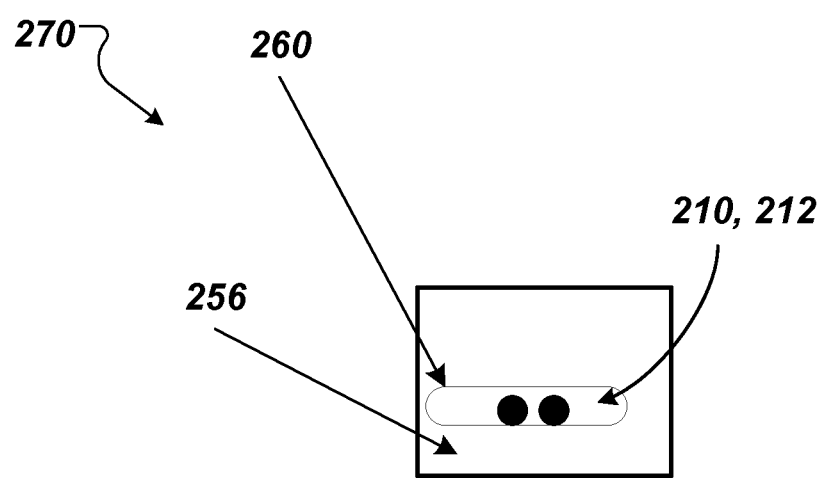
FIG. 5 shows another embodiment of how the disinfection sensor looks from the outer surface.
Figure 6:
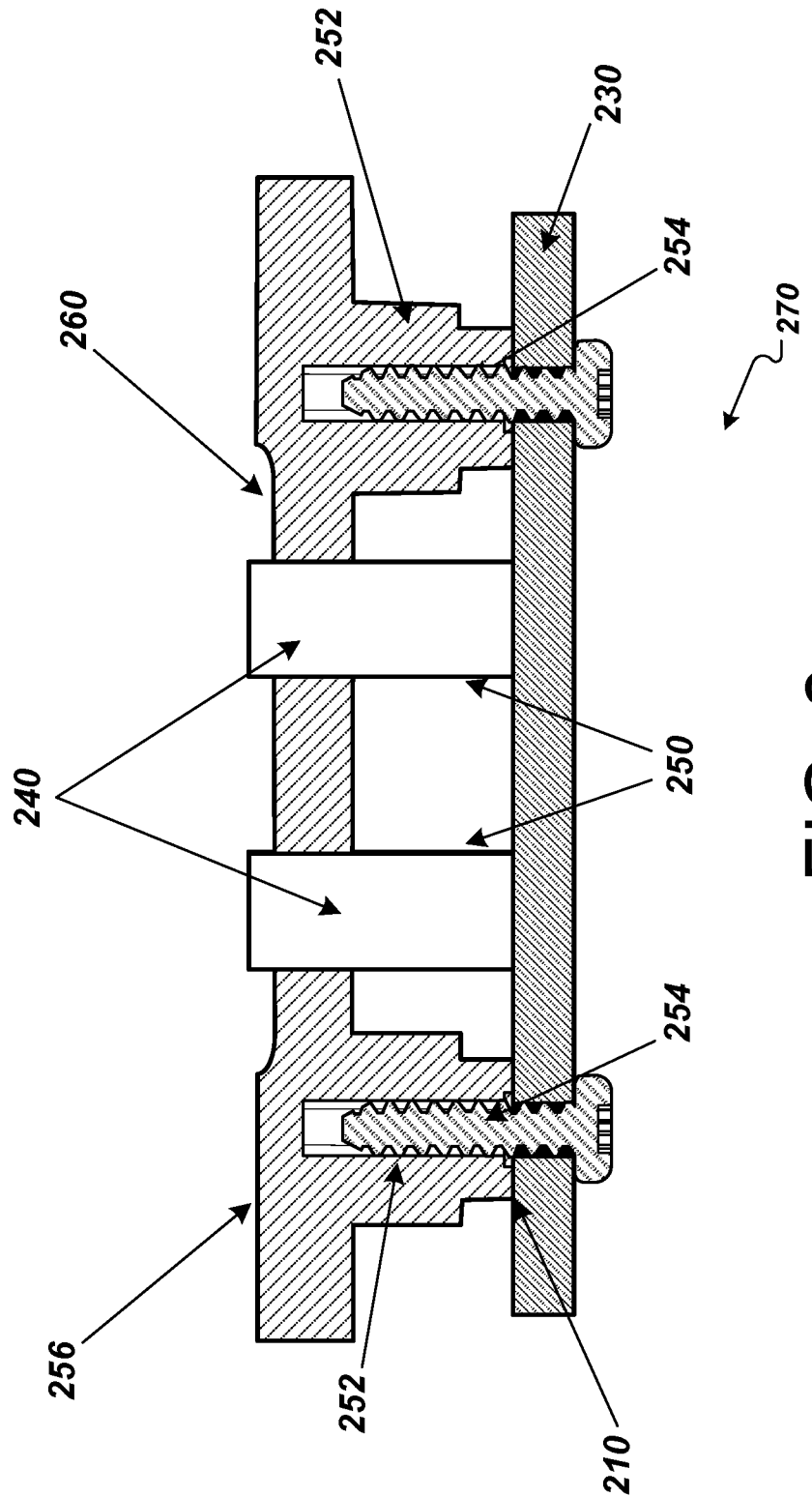
FIG. 6 shows a cross section of portions of the second embodiment of the disinfection sensor mounted at a surface to be disinfected.

FIGS. 5 and 6 show another configuration for mounting a disinfection sensor 270 as seen from the outer surface 256 and in cross-section, respectively. The disinfection sensor 270 is similar to the disinfection sensor 210 described above, and with like reference numbers referring to like parts. However, the disinfection sensor 270 includes an additional fluid channel 260 that is in the outer surface 256 of the machine 110 at the location 212 to be disinfected. The channel 260 is a blind hole and is located in fluid communication with the ends of the electrodes 240. The channel 260 is configured such that disinfecting fluid applied to the surface 256 will pool or become trapped in the channel 260. This configuration ensures that sufficient disinfecting fluid will be available to the electrodes 240 so that they can detect the presence of the disinfecting fluid (through wetness or conductivity change, or both). In some instances, the channel 260 can ensure that the disinfecting fluid present does not change its concentration over the dwell time stored in memory as necessary for successful disinfection of the outer surface 256. Although the channel 260 is illustrated as a single linear channel, other configurations are possible. For example, channels can intersect each electrode 240 of a disinfecting sensor 210 individually, or have a different shape than illustrated (e.g., a circle).

The information collected by the disinfecting sensors 210 can be used to determine and alert a user that a dialysis machine 110 is disinfected. The controller 150 can determine whether the proper disinfectant was used, the proper dwell time was used, the machine was disinfected in all specified locations, the machine was disinfected at the correct intervals, and that trained personnel disinfected the machine. The information stored in the machine could also be used for audit purposes.

A user interface can inform a user whether or not the machine is clean as determined by the disinfection sensors 210 and the controller 150. The indication of disinfection status for a particular location 212 can indicate "clean" or "not clean" for example. A particular location 212 can be indicated as "clean" if an appropriate disinfection fluid was detected for the appropriate dwell time, and within a given interval, such as hourly, time between treatments, end of the day. The machine's main display (as in FIG. 2A) can include a disinfection status as part of the user information displayed. The disinfection status can be displayed in multiple ways, e.g., a traffic light (red, yellow, green), a "not clean" light, or message indicating not disinfected, among others.

In some embodiments, disinfection status can be localized to each location 212. For example, a light such as an LED light can be integrated into each sensor 210 (e.g., on the circuit board 230). If the controller 150 has determined that a particular disinfection location 212 is clean or dirty, the light can change status, for example, by toggling on or off, or by changing color. In some instances, when the sensor 210 detects the presence of disinfection liquid (by conductivity change and/or by wetness) the light at that sensor location can change to indicate the start of disinfection and the end of disinfection. For example, the light change may be turning on or off, or changing color.

In some embodiments, the memory within the controller 150 can include recommended machine-cleaning intervals. The machine can warn users that the machine, or parts of the machine, needs cleaning. The recommended cleaning intervals can be different for differing locations 212. The machine can log when the disinfections occurred (between treatments, at the end of the day, at the beginning of the day, etc.). In some instances, the machine can log who conducted the disinfection, for example, requiring a user typing a pin code, a card reader, facial recognition, etc. The information can also be stored and supplied if an audit of disinfection practices is conducted.

The machine can give an indicator such as an alarm and require proper disinfection protocol be implemented, ensuring that staff follow training on cleanliness protocols. In some instances, the controller 150 can prevent use of the machine if it is determined to be not clean.

Figure 7:
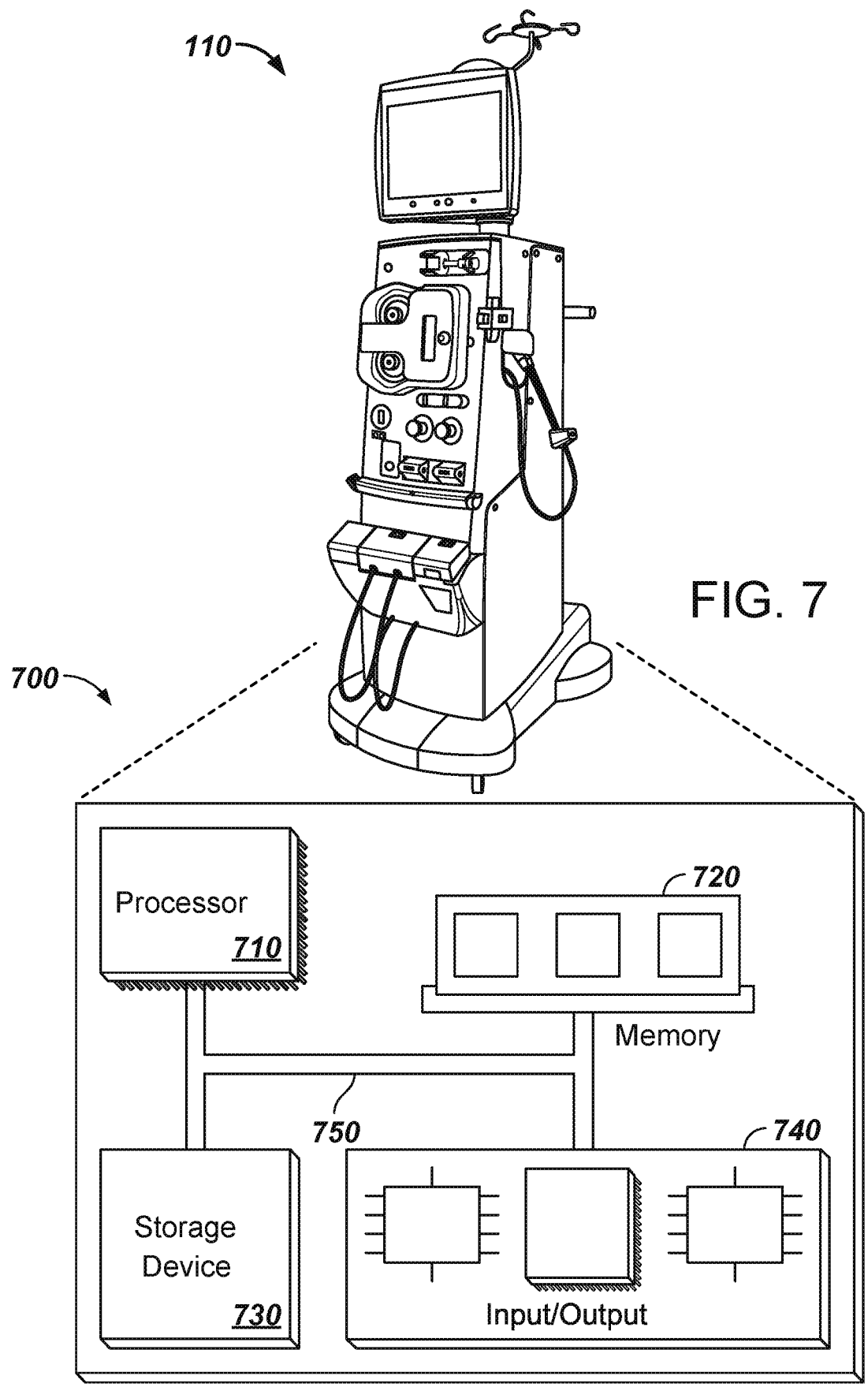
FIG. 7 shows a block diagram of an example computer system.
Figure 8:
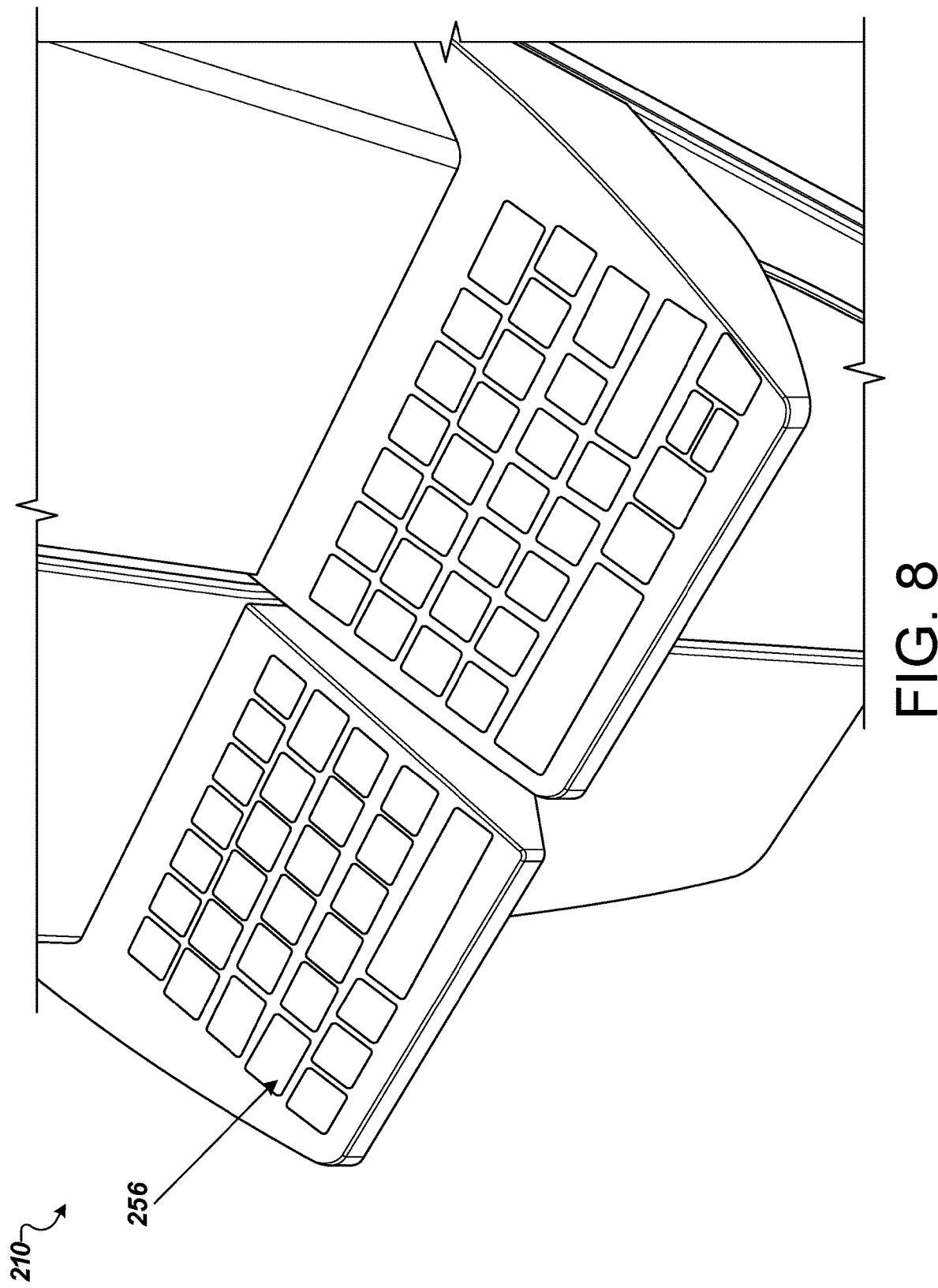
FIG. 8 shows an integrated capacitive touchscreen.

FIG. 7 shows a block diagram of an example computer system 700. For example, the controller described above with respect to FIG. 1 could be an example of the system 700 described here. Thus, the system 700 may be part of the dialysis machine of FIG. 1, and may be configured to assist in managing disinfection information. For example, the system 700 may determine information related to disinfection and be used to view alarms, logs, etc. related to such disinfection.

The system 700 includes a processor 710, a memory 720, a storage device 730, and an input/output device 740. Each of the components 710, 720, 730, and 740 can be interconnected, for example, using a system bus 750. The processor 710 is capable of processing instructions for execution within the system 700. The processor 710 can be a single-threaded processor, a multi-threaded processor, or a quantum computer. The processor 710 is capable of processing instructions stored in the memory 720 or on the storage device 730. The processor 710 may execute operations such as causing the dialysis system to carry out functions related to a dialysis treatment and determining information related to disinfection.

The memory 720 stores information within the system 700. In some implementations, the memory 720 is a computer-readable medium. The memory 720 can, for example, be a volatile memory unit or a non-volatile memory unit. In some implementations, the memory 720 stores information related to a treatment to be administered to a patient and information (e.g., logs) related to past and/or current disinfections.

The storage device 730 is capable of providing mass storage for the system 700. In some implementations, the storage device 730 is a non-transitory computer-readable medium. The storage device 730 can include, for example, a hard disk device, an optical disk device, a solid-date drive, a flash drive, magnetic tape, or some other large capacity storage device. The storage device 730 may alternatively be a cloud storage device, e.g., a logical storage device including multiple physical storage devices distributed on a network and accessed using a network. In some implementations, the information stored on the memory 720 can also or instead be stored on the storage device 730.

The input/output device 740 provides input/output operations for the system 700. In some implementations, the input/output device 740 includes one or more of network interface devices (e.g., an Ethernet card), a serial communication device (e.g., an RS-232 10 port), and/or a wireless interface device (e.g., a short-range wireless communication device, an 802.11 card, a 3G wireless modem, or a 4G wireless modem). In some implementations, the input/output device 740 includes driver devices configured to receive input data and send output data to other input/output devices, e.g., a keyboard, a printer, and display devices (such as the touch screen 106). In some implementations, mobile computing devices, mobile communication devices, and other devices are used. In some implementations, the system 700 is a microcontroller. A microcontroller is a device that contains multiple elements of a computer system in a single electronics package. For example, the single electronics package could contain the processor 710, the memory 720, the storage device 730, and input/output devices 740.

Although an example processing system has been described in FIG. 7, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

In some embodiments, the device can make use of touch screens. There are several touch screen technologies, one of them being capacitive. A capacitive touchscreen panel has an insulator, such as glass, coated with a transparent conductor, such as indium tin oxide (ITO). As the human body is also an electrical conductor, touching the surface of the screen results in a distortion of the screen's electrostatic field. The distortion in the electrical field caused by a person touching the surface of the screen is measurable as a change in capacitance. Different technologies may be used to determine the location of the touch. The location is then sent to the controller 150 for processing.

Different disinfecting fluids are also electrical conductors. The conductivity of the different disinfectant can have different levels of conductivity, causing the distortion of the screen's electrostatic field to change depending on the conductivity of the fluid that is placed on it. Furthermore, small channels that collect fluid (e.g., channel 260) can be placed near the capacitive touch screen so that a known amount of fluid collects in them. The channels would have to be easily cleanable.

FIG. 9 is an example of an integrated capacitive touchscreen. A clear shelf is built into the door, with a pocket that the capacitive touchscreen can sit in. The circuit board and batteries can sit under it and be accessible by a small plastic door. The capacitive touchscreen and the plastic shelf have similar optical properties and can be bonded together with an optical clear adhesive that has similar optical properties as the touch screen and shelf. The capacitive keyboard can be integrated into the door that can sense capacitance of the keyboard/touch screen itself and tell if keyboard capacitive touch is wetted.

Two electrodes 240 are shown in the figures, although there can be one, three, four or more such electrodes 240. Determining a conductivity measurement, using two, three, or four contacts depends on the cell constant. When determining a cell constant having a consistent amount of fluid to measure is factor, as is the spacing of the electrodes from each other. By having a small, accurate, cleanable channel molded into the plastic of the machine, a known amount of disinfectant can fill that channel, allowing for a repeatable cell constant and thus accurate conductivity measurements. Once a known conductivity is established, it can be compared to a table of disinfectants with known conductivities. With two electrodes, for example, the spacing between the center lines of the electrodes is known to a high degree of accuracy, as the volume of fluid captured in the channel. The size, material, surface finish, and other properties of the electrodes is known. Knowing these properties allows the cell constant to be determined. The channel can also be cleaned so that no residual fluid affects future measurements.

The repeatability of the fluid being measured influences the conductivity measurements when using a capacitor. The capacitor creates field lines, and if a channel is created next to the capacitor that is repeatable, the disruption of the field lines are repeatable as well, and thus measurable.

If specific conductivity is not important to the system's modality, then the system simply determines if the channel has been wetted, and for what period of time. In such an embodiment, the accuracy of the channel is less of a factor in determining the measurements.

A number of embodiments of the invention have been described. Nevertheless, it will be understood that various modifications may be made without departing from the spirit and scope of the invention. Accordingly, other embodiments are within the scope of the following claims.

What is claimed is:

1. A medical system, comprising:
a dialysis machine having at least one outside surface to be disinfected at a given location;
at least one disinfection sensor connected to the dialysis machine at the given location, the disinfection sensor comprising:
two or more electrodes in fluid contact with the outside surface of the dialysis machine, and
a conductivity sensor component in electrical contact with the two or more electrodes, the conductivity sensor component configured to send an electrical signal indicating a conductivity of a liquid on the outside surface of the dialysis machine and in contact with the two or more electrodes;
a processor configured to receive the electrical signal and thereby determine a disinfection status of the given location; and
a user interface configured to indicate the disinfection status of the given location.

2. The medical system of claim 1, wherein determining the disinfection status of the given location comprises determining if the electrical signal indicates the liquid on the outside surface of the dialysis machine is a disinfection fluid.

3. The medical system of claim 2, wherein determining if the electrical signal indicates the liquid on the outside surface of the dialysis machine is a disinfection fluid comprises comparing the electrical signal to conductivity signals stored in a memory connected to the processor.

4. The medical system of claim 2, wherein determining the disinfection status of the given location comprises determining a time interval the disinfection fluid is present on the outside surface of the dialysis machine.

5. The medical system of claim 4, wherein determining the disinfection status of the given location comprises comparing the time interval to a threshold time interval.

6. The medical system of claim 2, wherein determining the disinfection status of the given location comprises identifying the disinfection fluid present on the outside surface of the dialysis machine.

7. The medical system of claim 1, wherein the user interface is configured to alert a user that the dialysis machine needs cleaning.

8. The medical system of claim 1, further comprising a memory that stores a log of disinfections.

9. The medical system of claim 1, further comprising a cleanable channel on the outside surface of the dialysis machine that collects a known amount of the liquid.

10. A method comprising:
receiving, at a processor, a signal from a conductivity sensor indicating a conductivity of a liquid on an outside surface of a dialysis machine at a given location and in fluid contact with an electrode of the conductivity sensor;

determining a disinfection status of the outside surface at the given location; and displaying, on a user interface, the disinfection status of the outside surface at the given location.

11. The method of claim 10, wherein determining the disinfection status of the given location comprises determining if the signal indicates the liquid on the outside surface of the dialysis machine is a disinfection fluid.

12. The method of claim 11, wherein determining if the signal indicates the liquid on the outside surface of the dialysis machine is a disinfection fluid comprises comparing the signal to conductivity signals stored in a memory connected to the processor.

13. The method of claim 12, wherein determining the disinfection status of the given location comprises determining a time interval the disinfection fluid is present on the outside surface of the dialysis machine.

14. The method of claim 13, wherein determining the disinfection status of the given location comprises comparing the time interval to a threshold time interval.

15. The method of claim 12, wherein determining the disinfection status of the given location comprises identifying the disinfection fluid present on the outside surface of the dialysis machine.

16. The method of claim 10, comprising alerting a user that the dialysis machine needs cleaning.

17. The method of claim 10, comprising storing a log of disinfections in a memory.

* * * * *